(12) United States Patent
Van Gansbeghe et al.

(10) Patent No.: US 6,489,508 B1
(45) Date of Patent: Dec. 3, 2002

(54) METHOD FOR PURIFYING LACTIC ACID

(75) Inventors: Frederic Van Gansbeghe, Brussels (BE); Jean-Christophe Bogaert, Gijzegem (BE); Etienne Malhaize, Ceroux-Mousty (BE); Martin Van Gansberghe, La Hulpe (BE); Florence Wolff, Brussels (BE)

(73) Assignee: Brussels Biotech, Brussels (BE)

( * ) Notice: Subject to any disclaimer, the term of this patent is extended or adjusted under 35 U.S.C. 154(b) by 0 days.

(21) Appl. No.: 09/432,684

(22) Filed: Nov. 2, 1999

(Under 37 CFR 1.47)

Related U.S. Application Data

(63) Continuation of application No. PCT/BE98/00080, filed on Jun. 5, 1998.

(30) Foreign Application Priority Data

Jun. 6, 1997 (BE) .............................................. 9700489

(51) Int. Cl.⁷ .............................................. C07C 59/08

(52) U.S. Cl. ....................................... 562/589; 562/608
(58) Field of Search .................................. 562/608, 589

(56) References Cited

U.S. PATENT DOCUMENTS

| 1,594,843 | A | * | 8/1926 | Lawrie |
| 2,092,494 | A | * | 7/1937 | Bass .......................... 260/122 |
| 5,210,294 | A | * | 5/1993 | Mantovani et al. .......... 562/580 |

* cited by examiner

Primary Examiner—Mukund J. Shah
Assistant Examiner—Zachary C. Tucker
(74) Attorney, Agent, or Firm—Ladas & Parry

(57) ABSTRACT

The invention concerns a method for recuperating and purifying a lactic acid solution obtained initially from a fermentation medium or any other source, consisting in a pre-treatment to eliminate the ion loads capable of catalysing the lactic acid condensation and based on the principle of ion exchange or any other related principle, followed by at least a step of concentration at low temperature and brief retention time and at least a step of distilling the lactic acid using a thin layer process.

11 Claims, 2 Drawing Sheets

Figure 1:
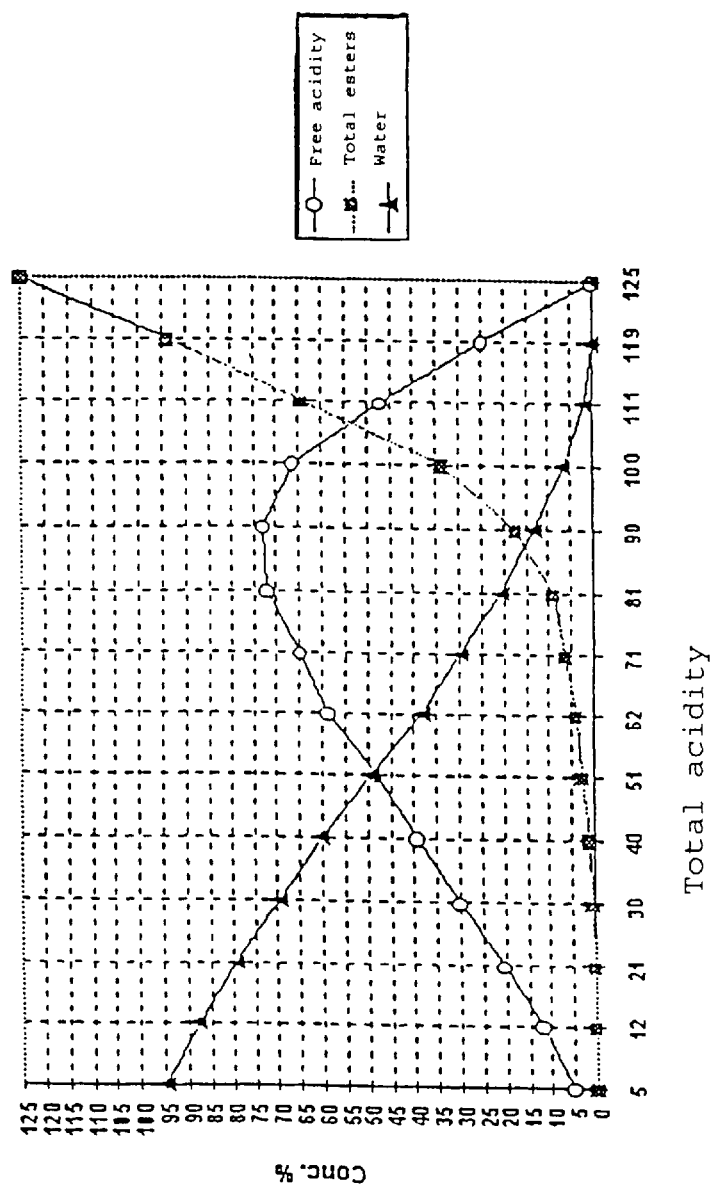

Figure 1 : Relationship between the total acidity and the concentration of the aqueous solution of lactic acid: (O) monomeric lactic acid, (□) oligomers of the n-lactoyllactic type, and concentration by weight of water (Δ).

METHOD FOR PURIFYING LACTIC ACID

This is a continuation of PCT/BE98/00080, filed Jun. 5, 1998.

FIELD OF THE INVENTION

Lactic acid or 2-hydroxypropanoic acid is an α-hydroxylated carboxylic acid which can be produced by fermenting a variety of pure (glucose, sucrose, lactose, etc.) or impure (products of the hydrolysis of starch, molasses, milk serum, etc.) carbonaceous substrates using microorganisms such as bacteria of the genera Lactobacillus, Pediococcus, Lactococcus and Streptococcus, or certain fungi such as Rhizopus Oryzae. Other routes for obtaining lactic acid, by way of chemical transformations of reagents derived from petrochemistry, such as the hydrolysis of lactonitrile, which is itself obtained starting from acetaldehyde, the chlorination and hydrolysis of propionic acid, or else via the nitration of propene, are known to the skilled person.

Lactic acid exists in two diastereoisomeric forms: L(+) and D(−) lactic acid, and finds novel applications every day, from the conventional use as a food preservative through to novel developments such as the synthesis of solvents, pesticides, herbicides, biodegradable polymers, etc. However, because of the increasing stringency of the quality criteria demanded and the necessity of achieving production costs which are compatible with the market, it is crucial to develop purification techniques which are efficient and inexpensive.

Lactic acid can be purified by precipitation in the form of metallic lactates, followed by a neutralization reaction using sulphuric acid (Maesato K., Komori A., Taki Chem. Co., JP 6,272,646 (Sep. 25, 1985)), or by esterification with an alcohol, distillation and hydrolysis of the ester which has been formed (Boroda T. A., Polovko V. N., Chistyakova E. A., Pishch.Prom. 1966, 4, 35–8), or by electrodialysis (Jacquement J. C., Rhone-Poulenc, DE 1,957,395 (Nov. 14, 1968)). The first of these processes suffers from the product being of poor quality and there being heavy losses of lactic acid, while the other two suffer from the fact that their cost is prohibitive. A more recent purification process consists in extracting the lactic acid by liquid/liquid extraction using at least one in water non-miscible organic solvent in the presence or absence of at least one Lewis base such as a tertiary amine. In accordance with this process, the lactic acid has to be recovered in a second step by means of carrying out a liquid/liquid back extraction. This step transfers the lactic acid back into the water. (Baniel A. M., Blumberg R., Hadju K., IMI, DE 2,329,480 (Jun. 19, 1972); Baniel A. M., Miles Lab., EP 49,429 (Oct. 06, 1980)). Finally, the lactic acid, in acid form and/or in the form of ammonium lactate or metallic lactate, can be purified by passing it through cationic and/or anionic ion exchange columns (Napierala W., Siminski M., Przem. Ferment. Rolny. 1972, 16(12), 4–10; Shkurino O. V., Dauksha V. E., Khim-Farm.Zh. 1986, 20(10), 1375–77; Maesato K., Komori A., Taki Chem.Co., JP 6,272,646 (Sep. 25, 1985); Obara H., Shimadzu corp., JP 63,188,632 (Jan. 30, 1987); Obara H., Shimadzu Corp, JP 0,191,788 (Sep. 30, 1987); Zeleneva N. A., Ivanova E. V., Karpushina I. A., Gaevskaya M. V., Teoriya I Prakitika Sorbtsionnyki Protsessov, 1982, 67–69).

It is to be noted that all these purification procedures are generally carried out starting from dilute solutions of lactic acid in water. This is justified by the actual structure of lactic acid, which carries a hydroxyl function and a carboxylic acid group at one and the same time. Thus, the bifunctionality of lactic acid is responsible for condensation reactions which generate lactoyllactic, dilactoyllactic, trilactoyllactic, . . . (n-lactoyllactic) units, which are also termed lactic acid oligomers. While these condensation or oligomerization reactions tend towards an equilibrium, the probability of their occurring increases as the concentration of the starting aqueous solution is increased (Holten C. H., "Lactic acid: Properties and chemistry of lactic acid and derivatives", Verlag Chemie, 1971). FIG. 1 shows the equilibrium which exists between the monomeric form of lactic acid and the oligomers over the whole range of conceivable concentrations.

The condensation or oligomerization reactions of lactic acid in fact correspond to esterification reactions; they are catalysed by Brönsted and Lewis acids and bases. Consequently, in order to avoid or minimize the occurrence of these reactions, it is imperative to carry out at least one preliminary purification step for removing any traces of impurities which would be capable of catalysing the oligomerization. Furthermore, it is also recognized that temperature accelerates the formation of oligomers (Holten C. H., "Lactic acid: Properties and chemistry of lactic acid and derivatives", Verlag Chemie, 1971). This explains why lactic acid in aqueous solution has for a long time been regarded as a substance which is not particularly volatile and which cannot be distilled at 100° C. In actual fact, lactic acid condenses to form oligomers whose boiling point under atmospheric pressure is higher than 100° C. More recent studies on the distillation of lactic acid by steam distilling at 160–200° C. show that the substance can be distilled with yields which are of the order of 75 to 85%. However, these drastic conditions are detrimental to the quality of the product; it is impossible to avoid degradation and racemization. Noerdlinger (U.S. Pat. No. 924,494, DE 221,786 and DE 224,664) has proposed a variant of distilling by steam distillation. This technique consists in passing air or warm inert gas at high speed over the surface of a solution of lactic acid which has previously been freed of the water which it contains. However, the energy consumption and the low yields obtained result in the procedure being of low viability from the industrial point of view. For the sake of completeness, we may also point out that there have been reports of other equipment and arrangement profiles which make it possible, with a greater or lesser degree of success, to concentrate and distil lactic acid, which is in dilute solution in water, under reduced pressure in an evaporator which has a vaporization surface which is very large as compared with the volume of liquid involved (Sepitka A., Prumisi Potravin 13, 385 and 605 (1962) and 14, 45 and 82 (1963); Shishkini A. V., Domanskii I. V., U.S.S.R. 709,613 (May 10, 1977)).

The present invention consists of a process for purifying lactic acid in an aqueous solution, as obtained from a fermentation medium or any other source, which has been previously freed of solid compounds and/or biomass. The reader is referred to any method known to the skilled person, such as centrifugation, flocculation, microfiltration, etc., as far as the step of separating solid compounds is concerned. By contrast, the purification process described in this invention is original in the sense that it ensures that a very high quality of lactic acid is obtained, with a particularly high mass yield and a minimum consumption of energy. "Very high quality" is understood as meaning residual concentrations of mineral and organic impurities which are such that the purified lactic acid can be used for pharmaceutical applications in accordance with any of the current Pharmacopoeias. Moreover, the lactic acid which is purified by the process described in the present invention is thermo-stable, that is it remains colourless after a 2-hour heat treatment at 180° C. and retains the optical activity of the lactic acid employed (stereospecific process). "Mass yield" is understood as being the ratio, expressed in per cent, of the mass of purified lactic acid over the mass of lactic acid employed; these masses correspond to lactic acid concentrations of 100%. Applications which require lower purity can, of course, also be met by the technique which is proposed in the present invention. The quantitative and selective aspects of this purification process are ensured by jointly implementing (1) a pretreatment which is designed to remove substances which are capable of catalysing the lactic acid condensation reaction, (2) temperature, dwell-time and viscosity conditions which reduce the involvement of the same condensation reactions, and (3) temperature, dwell-time, viscosity, pressure and equipment profile conditions which make it possible to concentrate the lactic acid so as to achieve a concentration by weight of 100%, and to distil it.

DESCRIPTION OF THE INVENTION

Figure 2:
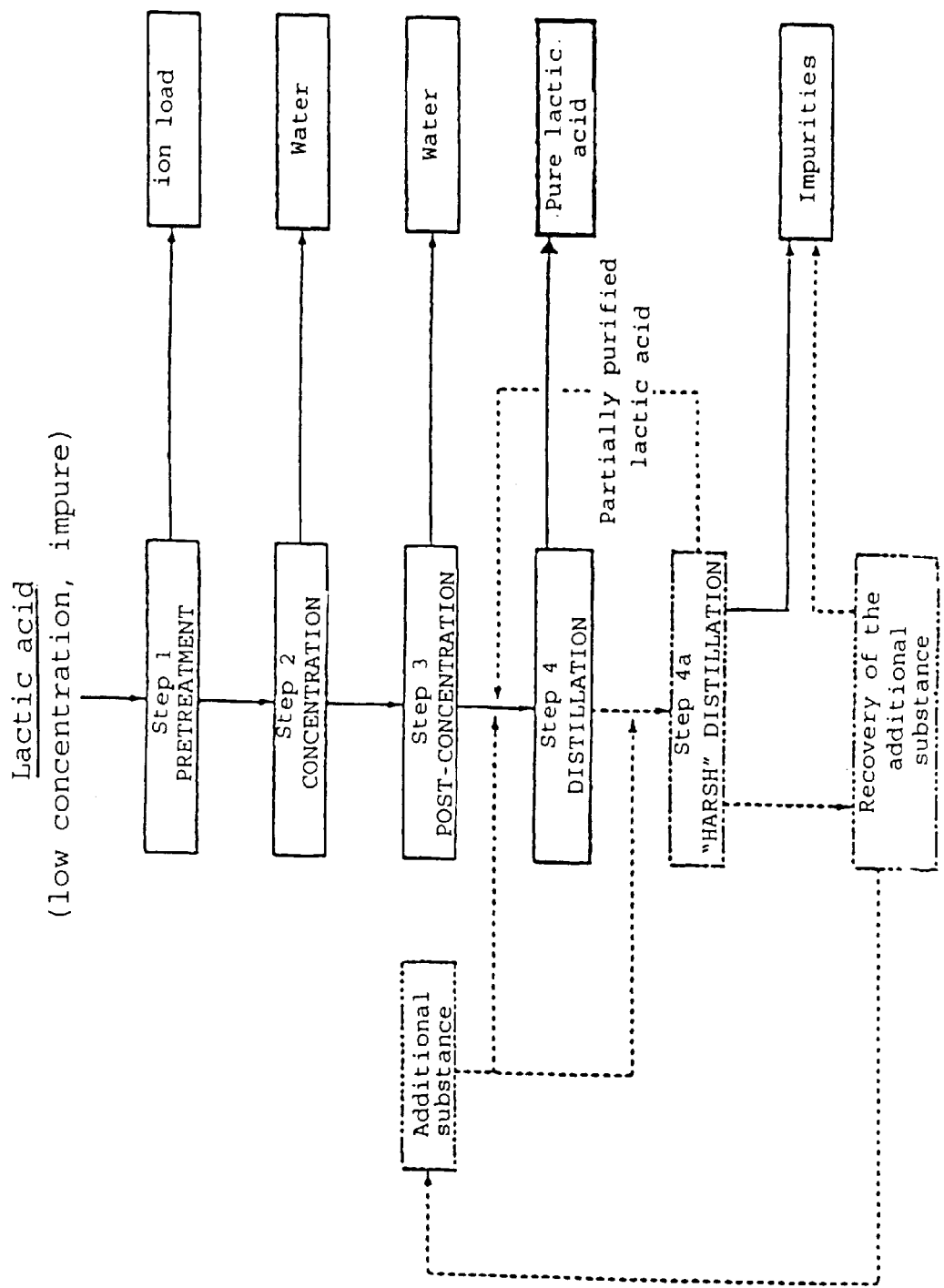

The present invention describes a process for purifying lactic acid which results from an aqueous solution of this acid, such as obtained from a fermentation medium or any other source which has been previously freed of the solid substances and/or biomass which may possibly have been present. FIG. 2 illustrates the lactic acid purification process to which the present invention refers. This process essentially comprises the following steps:

1. Pretreatment of the Dilute Solution of Lactic Acid (1)

The pretreatment under consideration within the context of the invention consists in removing ionic substances which are able to catalyse the condensation or oligomerization of the lactic acid. This pretreatment is carried out at a low concentration of lactic acid, that is at a concentration less than 80%, preferably less than 50% and still more preferably less than 30%. An approach which is favoured by the present invention consists in using ion exchange resins to remove the ionic substances. Thus, bringing the lactic acid solution into contact with an anion exchange resin which has previously been conditioned in basic form (OH⁻) enables the anionic impurities contained in the treated solution to be exchanged for hydroxide groups. The present invention does not stop at using solid anion exchange resins, but comprises any other technique known to the skilled person which makes it possible to remove anionic loads in favour of hydroxide ions, such as using fatty amines which are quaternized and which are present in ammonium hydroxide form in solution in at least one in water non-miscible organic solvent. In this case, the anion/hydroxide exchange takes place at the interface of the non-miscible phases and is followed by the phases being separated. A preferred approach of the invention consists, prior to carrying out the anion exchange step, in carrying out a treatment which is characterized by the lactic acid solution being freed of the monovalent, divalent, trivalent and/or polyvalent cationic loads which may be present. The cationic impurities are removed by bringing the lactic acid solution into contact with a cation exchange resin which has previously been conditioned in acid medium (H⁺). This approach is preferred insofar it avoids the formation and precipitation of metallic hydroxides, which are of low solubility in water, during the anionic treatment. Here, too, the invention is not limited to cation exchange resins but extends to any other technique known to the skilled person which is able to exchange the cations which are present in the lactic acid solution in favour of protons. The reader is referred, for example, to the use of a fatty acid of the carboxylic or sulphonic type which is dissolved in at least one in water non-miscible organic solvent. The cation/proton exchange takes place at the interface between non-miscible solvents and is followed by the phases being separated.

2. Concentration of the Lactic Acid Solution (2)

This step of the invention consists in concentrating, rapidly and at low temperature, the lactic acid solution, which has been previously treated by the method used as the first step of the invention (1), so as to achieve a concentration of between 50 and 90%, preferably between 70 and 90%. A preferred approach of the present invention envisages conducting this evaporation under reduced pressure, which is maintained between 50 and 500 mbar absolute, preferably between 50 and 250 mbar, in order to ensure that the solution boils at a temperature which is as low as possible. This step of the invention is carried out using any technique known to the skilled person, such as evaporation in a falling film.

3. Post-concentration of the Lactic Acid Solution (3)

This step post-concentrates the solution issuing from the apparatus used for step (2) up to a lactic acid concentration of 100%. The procedure can advantageously be carried out, using a minimal dwell-time and at a temperature which is as low as possible, in a mechanically shaken thin-film evaporator or using a short-path evaporator. The pressure is of the order of from 10 to 500 mbar, preferably between 50 and 300 mbar, and, still more preferably, between 50 and 150 mbar. The temperature of the heating wall of the body of the evaporator is adjusted so as to support the vaporization of the free water contained in the solution to be concentrated without, for all that, overheating this latter solution; that is a temperature which is between 50 and 150° C., preferably between 80 and 120° C. Surprisingly, it has been observed that, if the lactic acid is present quantitatively in the form of the lactic acid monomer (and in the absence of free water, concentration=100%), it is possible to distil it under reduced pressure in a reactor which maximizes the vaporization surface in relation to the volume of liquid. As well as claiming the use of such a reactor profile for distilling the lactic acid, the present invention guarantees that this concentrated acid is obtained quantitatively, in the form of distillable monomer, prior to its actual purification by distillation.

4. Purification of the Lactic Acid by Distillation (4)

This step is characterized by the demineralized and concentrated lactic acid solution, as produced in steps (1) to (3), being subjected to conditions such that the monomer (and, to a lesser extent, the dimer) of this acid is/are distilled quantitatively and selectively. "Quantitatively" is understood as meaning that the entirety of the distillable fraction is efficiently distilled. "Selectively" is understood as meaning that only the monomer (and to a lesser extent the dimer) of the lactic acid is/are distilled, without entraining impurities or degradation products. This step is advantageously conducted in a reactor which maximizes the vaporization surface in relation to the volume of liquid, that is by a reactor which exploits the properties of the thin film. A preferred approach of the present invention consists in using a mechanically shaken thin-film evaporator, on the outside of which the purified lactic acid is condensed, or a short-path evaporator, possessing an internal condenser, for distilling 100% lactic acid. The skilled person is familiar with the fact that such a system maximizes the heat-exchange surface and the vaporization surface. The temperature of the wall is maintained at between 50 and 180° C., preferably between 80 and 160° C., more preferably still between 110 and 160° C. The pressure is between $10^{-3}$ and $10^{+2}$ mbar absolute, preferably between $10^{-1}$ and $2.10^{+1}$ mbar absolute, still more preferably between 1 and 10 mbar. A preferred approach of the present invention is that of arranging the evaporator vertically, enabling the film to move forward under the combined impetus of mechanical shaking and gravity. According to a variant, which represents an improvement, which is not essential for the present invention, the purification residue can be conducted towards a second still in which the temperature and pressure conditions are more drastic (FIG. 2, step 4a). The lactic acid which is supplied from this post-distillation, and which is partially purified, can be recycled either towards feeding the main still (step 4) or upstream of the process. A preferred version of the present invention is that of adding an additional substance which is intended to facilitate the thin-layer flow and evaporation of the lactic acid during the distillation and/or post-distillation step(s). This additional substance comprises any non-toxic substance which is chemically inert vis-à-vis the lactic acid, which is of low volatility, which is thermostable and of low viscosity under the distillation and post-distillation conditions, and which is preferably non-miscible with the lactic acid in order to facilitate its separation by decantation and recycling. By way of example, we may mention that using paraffins such as Fina Vestan A80B, A180B and, preferably, A360B promoted the draining-off of impurities and evaporation of the lactic acid while at the same time meeting the abovementioned requirements. Other details and features of the invention, which are given below by way of non-limiting examples, are evident from the description, as are some possible forms of implementing it.

EXAMPLES

Example 1

Demineralization of a Lactic Acid Solution

A solution of lactic acid obtained by fermentation is demineralized by percolating it through solid ion exchange resins. The analysis of the fed-in solution is as follows: lactic acid, 185.1 g.l$^{-1}$, pH 2.25, sulphates, 1250 ppm, calcium, 929 ppm, iron, 15.8 ppm, potassium, 133 ppm, and sodium, 98 ppm. This solution is fed, at the rate of 3 BV/h, into the top of a column containing 1 BV of BAYER Lewatit S 2528 macroporous strong-cation resin having a crosslinked polystyrene structure, which resin has previously been conditioned in H$^+$form by the passage of 120 g of pure hydrochloric acid per litre of resin in the form of a 6% solution. The effluent which is collected at the outlet of this column is then conducted towards a column which contains the same volume of anionic resin of average basicity, which is formed from ternary and quaternary amine groups which are grafted onto a polystyrene structure which is marketed by BAYER under the reference Lewatit S 4328. This resin is previously conditioned in basic form by percolating through it 120 g of pure sodium hydroxide in the form of a solution having a concentration of 4%. After treatment of a volume of the solution corresponding to 15 times the volume of the cationic resin, the average analysis of the lactic acid solution which has been treated under these conditions is as follows: lactic acid, 167 g.l$^{-1}$, pH 1.75, sulphates, 0.7 ppm, calcium, 0.8 ppm, iron, 0.3 ppm, potassium, 1.1 ppm, and sodium, 0.9 ppm. Breakthrough of the cationic resin, which is expressed in an increase in the concentration of monovalent cations in the effluent from the first column of the system occurred after the passage of 15 BV of lactic acid solution. Breakthrough of the anionic resin, as demonstrated by detecting sulphate ions in the effluent from the second column of the system, occurred after treating 18 BV of the fed-in solution.

Example 2

Concentration of a Lactic Acid Solution to a Value of 80%

A solution which has been treated in accordance with Example 1 is fed continuously into a stainless steel falling-film evaporator having an evaporation surface area of 0.31 m$^2$. The concentrated lactic acid solution is removed at the same rate as the rate at which the system is fed (10.45 l.h$^{-1}$) in order to maintain a constant level in the system. Heating of the wall is ensured by circulating heat-exchanging oil in a double jacket. The pressure and temperature conditions, and the concentrations obtained, are shown in Table 1 below.

TABLE 1

Concentration of an 18.5% by weight aqueous solution of lactic acid in an evaporator of the falling-film type having an evaporation surface area of 0.31 m$^2$.

| Pressure (mbar) | Temperature (° C.) | Concentration aimed at (% by wt.) | Concentration[1] obtained (% by wt.) | Δconcentration (% by wt.) |
|---|---|---|---|---|
| 98 | 46.9 | 70 | 68.3 | −1.7 |
| 102 | 47.2 | 70 | 71.7 | 1.7 |
| 204 | 68.3 | 70 | 70.2 | 0.2 |
| 100 | 21.8 | 75 | 74.4 | −0.6 |
| 103 | 56.4 | 80 | 79.6 | −0.4 |
| 101 | 69 | 85 | 84.6 | −0.4 |
| 197 | 82.6 | 85 | 86.5 | 1.5 |
| 96 | 68.3 | 85 | 82.1 | −2.9 |

[1]the concentration or total acidity is determined by means of acid-base titration following saponification.

Example 3

Post-concentration of Lactic Acid at Various Pressures

An 81.75% by weight solution of lactic acid (level of polymerization=13.19%) is fed continuously into a mechanically shaken UIC thin-film borosilicate glass evaporator which has an internal (short-path) condenser and which exhibits heating and condensation surface areas of 0.06 m$^2$ in size, which evaporator is preceded by a degasifier-preheater whose temperature is adjusted by circulating heat-exchanging oil. The whole is maintained under a pressure of from 50 to 250 mbar absolute. The results shown in Table 2 were obtained using a wall temperature of 100° C., a degassing temperature of 80° C., a condenser temperature of 15° C., a rotation speed of the rotor of 400 rpm (revolutions per minute) and a feeding rate of 1000 g.h$^{-1}$.

TABLE 2

Post-concentration of an 81.75% by weight lactic acid solution in an evaporator of the 0.06 m² UIC short-path type.

| Pressure (mbar) | Total acidity[1] concentrate (% by wt.) | Total acidity[1] condensate (% by wt.) | Level of[2] polymerization concentrate (%) | Yield (%) |
|---|---|---|---|---|
| 50  | 100.8 | 46.1 | 15.5 | 70.7 |
| 100 | 101.8 | 12.1 | 14.4 | 96.2 |
| 150 | 101.5 | 8.4  | 14.2 | 97.9 |
| 200 | 99.7  | 6.9  | 12.9 | 95.9 |
| 250 | 100.2 | 6.5  | 13.6 | 97.6 |

[1]total acidity is determined by means of acid-base titration following saponification.
[2]the level of polymerization is defined as being the ratio of the esterified acidity (percentage by weight of carboxylic acid group in ester form) over the total acidity.

Example 4

Influence of Dwell-time at High Temperature on the Level of Polymerization (in a Static System)

A demineralized lactic acid solution as obtained in Examples 1, 2 and 3, whose concentration is 98.1% by weight (level of polymerization=13.1%), is kept at 100° C. and atmospheric pressure for varying periods of time. Table 3 shows the dependence of the level of polymerization on the dwell-time.

TABLE 3

Influence of dwell-time at high temperature on the level of polymerization of a lactic acid solution having a total acidity of 98.1% by weight.

| Dwell-time (min) | Free acidity[1] (% by weight) | Level of polymerization[2] (%) |
|---|---|---|
| 0    | 85.9 | 12.5 |
| 60   | 83.9 | 14.5 |
| 120  | 81.7 | 16.7 |
| 240  | 74.9 | 23.7 |
| 1050 | 65.0 | 33.8 |
| 1395 | 64.0 | 34.8 |

[1]the free acidity is determined by acid-base titration.
[2]the level of polymerization is defined as the ratio of the esterified acidity over the total acidity, which is 98.1% by weight.

Example 5

Influence of Dwell-time on the Level of Polymerization (in a Dynamic System)

A lactic acid solution having a concentration equal to 102% by weight, and which is obtained in a similar manner to that described in the first three examples of the present invention, is fed at a constant rate into a mechanically shaken UIC thin-film borosilicate glass evaporator which has an internal (short-path) condenser and which exhibits heating and condensation surface areas of 0.06 m² in size. The system is maintained under a pressure of 40 mbar absolute, with the condenser temperature and the wall temperature being respectively adjusted to 18° C. and 160° C. (Table 4). It is assumed, in this connection, that, if all the other parameters remain constant, the dwell-time in the apparatus in contact with the heated wall increases when the rate of feeding decreases.

TABLE 4

Influence of temperature on the level of polymerization of a 102% by weight solution of lactic acid in an evaporator of the 0.06 m² UIC short-path type.

| Flow rate (g/h) | Total acidity (% by wt.) | % n-mer[1] (%) |||||
|---|---|---|---|---|---|---|
| | | mono- | di- | tri- | tetra- | penta- |
| 510 | 111.9 | 2.9 | 50.4 | 33.1 | 10.7 | 2.9 |
| 740 | 112.1 | 3.1 | 57.0 | 28.5 | 8.8  | 2.6 |
| 870 | 109.7 | 3.4 | 60.9 | 27.0 | 8.6  | 0.0 |

[1]the percentage of n-mers is determined by gel permeation chromatography (GPC).

Example 6

Influence of Temperature on the Level of Polymerization

A solution of lactic acid having a concentration equal to 102% by weight, and which was obtained in a manner similar to that described in the first three examples of the present invention, is fed at a constant rate into a mechanically shaken UIC thin-film borosilicate glass evaporator which has an internal (short-path) condenser and which exhibits heating and condensation surface areas of 0.06 m² in size. The system, which is fed at the rate of 730 g.h$^{-1}$, is maintained under a pressure of 40 mbar absolute. The temperature of the condenser is maintained at 18° C. (Table 5).

TABLE 5

Influence of the temperature on the level of polymerization in a 0.06 m² UIC short-path evaporator.

| Temperature (° C.) | Total acidity (% by wt.) | % n-mer[1] (%) |||||
|---|---|---|---|---|---|---|
| | | mono- | di- | tri- | tetra- | penta- |
| 140 | 108.5 | 17.4 | 52.3 | 21.7 | 8.5 | 0.0 |
| 150 | 107.8 | 7.1  | 62.8 | 21.9 | 6.1 | 2.4 |
| 160 | 109.3 | 3.1  | 57.0 | 28.5 | 8.8 | 2.6 |

[1]the percentage of n-mer is determined by means of gel permeation chromatography (GPC)

Example 7

Distillation of Lactic Acid, and Influence of the Level of Polymerization on the Distillation Yield and the Quality of the Distillate The lactic acid solutions, as obtained from Example 4, are introduced at a constant rate into a mechanically shaken UIC thin-film borosilicate glass evaporator which has an internal (short-path) condenser and which exhibits heating and condensation surface areas of 0.06 m² in size, which evaporator is preceded by a degasifier-preheater whose temperature is adjusted by circulating heat-exchanging oil. The whole is maintained under a pressure of 5 mbar absolute. Table 6 records the results obtained using a wall temperature of 140° C., a degassing temperature of 80° C., a condenser temperature of 15° C., a rotational speed of the rotor of 400 rpm (revolutions per minute) and a feeding rate of between 798 and 915 g.h$^{-1}$. The coloration of the resulting distillates is regarded as being representative of their chemical purity.

TABLE 6

Influence of the level of polymerization on the distillation yield and the quality of the distillates (evaporator of the 0.06 m² UIC short-path type)

| Level of polymerization of the fluid employed (%) | Mass yield (%) | Total acidity distillates (% by wt.) | Level of polymerization distillates (%) | Coloration[1] (Hazen) |
|---|---|---|---|---|
| 14.5 | 89.8 | 96.5 | 4.1 | 0 |
|  | 81.5 | 97.9 | 6.5 | 0 |
| 16.7 | 82.1 | 96.8 | 5.7 | 0 |
|  | 76.4 | 97.0 | 6.6 | 0 |
| 23.7 | 66.3 | 96.2 | 7.6 | 20 |
|  | 64.6 | 95.3 | 7.1 | 20 |
| 33.8 | 64.8 | 96.5 | 9.5 | 70 |
| 34.8 | 43.8 | 94.9 | 9.4 | 275 |

[1]the coloration is determined in accordance with the APHA (American Public Health Association) standard.

Example 8

Distillation of Lactic Acid and Influence of the Ionic Load on the Distillation Yield Concentrated sulphuric acid (98%) is added deliberately to a demineralized lactic acid solution which is as obtained in Examples 1, 2 and 3 and whose concentration is 101.46% by weight. This solution is then introduced continuously into a mechanically shaken UIC thin-film borosilicate glass evaporator which has an internal (short-path) condenser and which exhibits heating and condensation surface areas of 0.06 m² in size, which evaporator is preceded by a degasifier-preheater whose temperature is adjusted by circulating heat-exchanging oil (Table 7). The whole is maintained under a pressure of 3.5 mbar absolute. The conditions imposed on the system are as follows: wall temperature: 130° C., degassing temperature: 84° C., condenser temperature: 10° C., rotary speed of the rotor: 400 rpm (revolutions per minute).

TABLE 7

Effect of adding sulphuric acid to a lactic acid solution on the distillation yield in a 0.06 m² UIC short-path evaporator.

| Content[1] of exogenous protons (mmol/kg) | Content[1] of exogenous sulphate ions (ppm) | Flow rate (g/h) | Mass yield (%) | Entrainment[2] at the degasifier (% by wt.) |
|---|---|---|---|---|
| 0 | 0 | 622 | 65.2 | 14.2 |
|  |  | 625 | 66.6 |  |
|  |  | 623 | 68.0 |  |
| 2.1 | 100 | 630 | 64.6 | 15.6 |
|  |  | 631 | 65.8 |  |
|  |  | 630 | 69.3 |  |
| 5.2 | 200 | 626 | 68.7 | 14.6 |
|  |  | 585 | 69.6 |  |
| 8.3 | 400 | 623 | 68.0 | — |
|  |  | 618 | 68.5 |  |
|  |  | 622 | 69.6 |  |
| 12.5 | 600 | 639 | 46.1 | 75.7 |
|  |  | 640 | 45.3 |  |
| 24.0 | 1150 | 644 | 43.6 | — |
|  |  | 647 | 37.8 |  |

[1]"exogenous" is understood as meaning ions (protons and sulphates) which are introduced deliberately.
[2]entrainment at the degasifier denotes the percentage of the mass employed which is collected at the degasifier following droplet entrainment.

Example 9

Distillation of Lactic Acid and Influence of Temperature on the Distillation Yield and on the Quality of the Distillate A lactic acid solution whose concentration is equal to 98.12% by weight and which is obtained in a similar manner to that described in the first three examples of the present invention is fed at a constant rate into a mechanically shaken UIC thin-film borosilicate glass evaporator which has an internal (short-path) condenser and which exhibits heating and condensation surfaces of 0.06 m² in size. The system, which is fed at the rate of 870 g.h$^{-1}$, is maintained under a pressure of 5 mbar absolute. The temperature of the condenser is maintained at 15° C. by circulating water, while that of the degasifier is maintained at 80° C. by circulating heat-exchanging oil (Table 8).

TABLE 8

Influence of temperature on the distillation yield and on the quality of the distillate in an evaporator of the 0.06 m² UIC short-path type.

| Wall temperature (° C.) | Mass yield (%) | Coloration[1] (Hazen) |
|---|---|---|
| 130 | 79.2 | <5 |
| 140 | 82.7 | <5 |
| 150 | 88.9 | 70 |

[1]The coloration is determined in accordance with the APHA standard.

Example 10

Distillation of Lactic Acid and Influence of the Dwell-time on the Quality of the Distillate The same 98.12% by weight lactic acid solution, and the same experimental conditions as used for Example 9, are employed once again for two different feeding rates, of 870 and 1120 g.h$^{-1}$, respectively, and using a wall temperature of 150° C. As in the case of Example 5, it is assumed that the dwell-time in the apparatus varies inversely with the feeding rate.

TABLE 9

Influence of the feeding rate on the distillation yield and the quality of the distillate in an evaporator of the 0.06 m² UIC short-path type.

| Feeding rate (g/h) | Mass yield (%) | Coloration[1] (Hazen) |
|---|---|---|
| 870 | 88.9 | 70 |
| 1120 | 85.5 | 20 |

[1]The coloration is determined in accordance with the APHA standard.

What is claimed is:
1. A process for recovering and purifying an aqueous solution of lactic acid comprising the steps of:
   a) pretreating a diluted solution of lactic acid to remove ionic substances which are able to catalyze polycondensation, wherein cationic impurities are fixed by exchange for hydrogen on a resin in the hydrogen form while lactic acid is percolated through and wherein subsequently anionic impurities are fixed by exchange for hydroxide groups on a resin in the hydroxide form while lactic acid is percolating through;
   b) concentrating and re-concentrating the diluted solution in a manner which reduces the risk of lactic acid polycondensation in order to produce a concentrated solution of lactic acid that does not contain free water; and c) distilling the concentrated solution of lactic acid obtained in step b) to obtain the purified lactic acid.

2. The process according to claim 1, wherein the diluted solution of lactic acid is concentrated and distilled using a thin-layer process.

3. The process according to claim 1, wherein step c) is effected using a mechanically shaken thin-film evaporator which is provided with an internal or external condenser and a heated wall.

4. The process according to claim 3, wherein the concentrated solution of lactic acid prepared in step b) is distilled using a thin-film evaporator under a pressure between $10^{-3}$ and $10^{+2}$ mbar absolute and the heated wall is at a temperature between 110 and 160° C.

5. The process according to claim 1, wherein the concentrated solution of lactic acid prepared in step b) comprises at least 1% to at most 20%, based on its weight, of an inert and non-miscible compound.

6. The process according to claim 1, further comprising distilling residue from step c) and recycling the concentrated solution of lactic acid.

7. The process according to claim 6, wherein the residue may comprise at least 1% to at most 20% based on its weight of an inert and non-miscible compound.

8. The process according to claim 1, wherein step b) is repeated twice in order to first obtain a lactic acid concentration between 50 and 90% by weight and then to obtain a lactic acid concentration of 100% by weight, under pressure conditions between 50 and 500 mbar absolute.

9. The process according to claim 1, further comprising a second concentration step carried out in a mechanically shaken thin-film evaporator provided with an internal or external condenser, under a pressure of between 10 and 500 mbar and wherein the heated wall of the thin-film evaporator is at a temperature of between 50 and 150° C.

10. The process according to claim 1, wherein before step a) the concentration of the diluted solution of lactic acid is less than 80% by weight.

11. The process according to claim 1, wherein the ionic substances comprise anionic and cationic impurities and are removed using solid or liquid ion exchange resins.

* * * * *

UNITED STATES PATENT AND TRADEMARK OFFICE
CERTIFICATE OF CORRECTION

PATENT NO.    : 6,489,508 B1
DATED         : December 3, 2002
INVENTOR(S)   : Frederic Van Gansberghe It is certified that error appears in the above-identified patent and that said Letters Patent is hereby corrected as shown below:

<u>Title page,</u>
Item [75], "Gansbeghe" should read -- Gansberghe --.

Signed and Sealed this

Fourth Day of March, 2003

JAMES E. ROGAN
*Director of the United States Patent and Trademark Office*